US008569702B2

(12) United States Patent
Johansen

(10) Patent No.: US 8,569,702 B2
(45) Date of Patent: *Oct. 29, 2013

(54) OPTICAL MULTIPHASE FLOWMETER

(75) Inventor: Espen S. Johansen, Houston, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/019,182

(22) Filed: Feb. 1, 2011

(65) Prior Publication Data

US 2011/0203386 A1 Aug. 25, 2011

Related U.S. Application Data

(63) Continuation of application No. 11/421,700, filed on Jun. 1, 2006, now Pat. No. 7,880,133.

(51) Int. Cl.
*G01F 1/00* (2006.01)

(52) U.S. Cl.
USPC ........................................ 250/356.1; 250/266

(58) Field of Classification Search
USPC ................ 50/356.1; 250/266, 356.1
See application file for complete search history.

(56) References Cited

U.S. PATENT DOCUMENTS

| 4,402,230 | A | * | 9/1983 | Raptis ........................ 73/861.04 |
| 4,815,843 | A | * | 3/1989 | Tiefenthaler et al. ......... 356/128 |
| 4,856,321 | A | * | 8/1989 | Smalling et al. ........... 73/40.5 A |
| 4,856,344 | A | | 8/1989 | Hunt |
| 5,025,160 | A | | 6/1991 | Watt |
| 5,167,149 | A | | 12/1992 | Mullins et al. |
| 5,201,220 | A | | 4/1993 | Mullins et al. |
| 5,654,551 | A | | 8/1997 | Watt et al. |
| 5,831,743 | A | | 11/1998 | Ramos et al. |
| 5,956,132 | A | | 9/1999 | Donzier |
| 6,023,340 | A | * | 2/2000 | Wu et al. ........................ 356/432 |
| 6,076,049 | A | | 6/2000 | Lievois et al. |

(Continued)

FOREIGN PATENT DOCUMENTS

| CA | 2403616 | 9/2001 |
| GB | 2266959 | 11/1993 |

(Continued)

OTHER PUBLICATIONS

GB Search Report for Application No. 0710273.4, dated Sep. 7, 2007.

(Continued)

*Primary Examiner* — Christine Sung
(74) *Attorney, Agent, or Firm* — Patterson & Sheridan, LLP

(57) ABSTRACT

Method and apparatus enable direct measurement of at least one flow velocity for one or more phases within a multiphase fluid mixture flowing in a conduit. Some embodiments provide determination of actual individual phase flow rates for three phases (e.g., oil, water and gas) that are distinct from one another within the fluid mixture. A multiphase flowmeter according to embodiments of the invention includes at least two optical sensors spatially distributed along a length of the conduit and designed to detect light interactions with the fluid mixture unique to the phases such that detected time-varying signals can be processed via cross-correlation or an array processing algorithm to provide desired individual phase flow velocity for oil, water and/or gas phases. This flow velocity can be applied to phase fraction measurements, which can be obtained utilizing the same flowmeter or another separate device, to calculate the flow rates for the phases.

18 Claims, 4 Drawing Sheets

(56) References Cited

U.S. PATENT DOCUMENTS

| | | | |
|---|---|---|---|
| 6,292,756 | B1 | 9/2001 | Lievois et al. |
| 6,354,147 | B1 | 3/2002 | Gysling et al. |
| 6,532,826 | B1 | 3/2003 | Dou |
| 6,611,319 | B2 * | 8/2003 | Wang ................................ 356/28 |
| 6,655,221 | B1 | 12/2003 | Aspelund et al. |
| 6,672,163 | B2 | 1/2004 | Han et al. |
| 6,683,681 | B2 | 1/2004 | DiFoggio et al. |
| 6,691,584 | B2 | 2/2004 | Gysling et al. |
| 6,850,317 | B2 * | 2/2005 | Mullins et al. ................... 356/70 |
| 6,945,095 | B2 | 9/2005 | Johansen |
| 6,997,055 | B2 | 2/2006 | DiFoggio |
| 7,142,306 | B2 | 11/2006 | Wu et al. |
| 7,281,415 | B2 | 10/2007 | Johansen |
| 7,542,142 | B2 | 6/2009 | Wu et al. |
| 7,880,133 | B2 | 2/2011 | Johansen |
| 2004/0113081 | A1 | 6/2004 | Hyde |
| 2004/0139791 | A1 | 7/2004 | Johansen |
| 2005/0188771 | A1 | 9/2005 | Lund Bo et al. |
| 2006/0186340 | A1 | 8/2006 | Lievois et al. |
| 2007/0044572 | A1 * | 3/2007 | Davis et al. ................. 73/861.42 |
| 2007/0064218 | A1 * | 3/2007 | Montgomery et al. ......... 356/28 |
| 2007/0278408 | A1 * | 12/2007 | Johansen ................... 250/341.7 |
| 2010/0000333 | A1 * | 1/2010 | Volker et al. ................ 73/861.95 |
| 2010/0016689 | A1 * | 1/2010 | Kanayama et al. ........... 600/316 |

FOREIGN PATENT DOCUMENTS

| | | |
|---|---|---|
| WO | 91/18280 | 11/1991 |
| WO | 2005/047908 | 5/2005 |
| WO | WO 2005047908 A1 * | 5/2005 |
| WO | 2007/009097 | 1/2007 |

OTHER PUBLICATIONS

British Examination Report dated Sep. 22, 2009.

Canadian Office Action for Application No. 2,590,996 dated Jul. 15, 2010.

Beck, M.S. "Correlation in Instruments: Cross Correlation Flowmeters," Journal of Physics E: Instrument Science Technology; vol. 14, pp. 7-19 (1981).

* cited by examiner

US 8,569,702 B2

OPTICAL MULTIPHASE FLOWMETER

CROSS-REFERENCE TO RELATED APPLICATIONS

This application is a continuation of U.S. patent application Ser. No. 11/421,700, filed Jun. 1, 2006 now U.S. Pat. No. 7,880,133, which is related to U.S. patent application Ser. No. 11/065,489 entitled "Multi-Channel Infrared Optical Phase Fraction Meter," filed Feb. 24, 2005, which are both herein incorporated by reference.

BACKGROUND OF THE INVENTION

1. Field of the Invention

Embodiments of the invention generally relate to methods and apparatus for determining at least one flow velocity/rate for one or more phases within a multiphase fluid flow.

2. Description of the Related Art

In the petroleum industry, as in many other industries, ability to monitor flow of certain fluids in process pipes in real time offers considerable value. Oil and/or gas well operators periodically measure water/oil/gas flow rates within an overall production flow stream containing a mixture of these three phases. This information aids in improving well production, allocating royalties, properly inhibiting corrosion based on the amount of water and generally determining the well's performance.

While some techniques enable measuring flow rates within two phase mixtures, difficulty arises in determining individual volumetric fractions and flow rates in three phase mixtures. Separators can be used to separate out one or more phases from the flow stream, but they introduce additional equipment and costs. Other costly and time consuming procedures entail manual sampling of the mixture to obtain information regarding the individual volumetric fractions. On the other hand, flowmetering devices can be complex and can restrict flow creating significant pressure loss, such as when venturi based measurements are required.

In many instances, multiphase flowmeters utilize a method to measure a flow rate of the entire flow stream and another process to measure volume fractions of oil, water and gas. This measured information when applied to flow models enables estimation of each of the individual phase flow rates. However, the flow models make assumptions regarding the flow characteristics such as by modeling with the flow model the slippage velocity between the liquid and gas phases. Therefore, the flow models cannot completely account for uniqueness of each particular fluid flow. In other words, application of these flow models with measured total flow and volume fractions does not permit direct measurement of actual phase velocities and flow rates independently.

Therefore, there exists a need for improved methods and apparatus that enable determining at least one flow velocity for one or more phases within a multiphase fluid flow and hence flow rate for the one or more phases.

SUMMARY OF THE INVENTION

Embodiments of the invention generally relate to methods and apparatus for determining at least one flow velocity/rate for one or more phases within a multiphase fluid flow. According to some embodiments, an apparatus for measuring flow of a fluid mixture in a conduit includes first and second optical sensors disposed along the conduit and configured to detect light interactions with the fluid mixture, wherein the first optical sensor is separated by a distance in a direction of flow through the conduit from the second optical sensor, and a processor coupled to receive first and second time-varying signals of the light interactions from the first and second optical sensors, respectively, wherein the processor is configured with logic to determine phase velocity of at least one phase within the fluid mixture. In some embodiments, a method of measuring flow of a fluid mixture in a conduit includes detecting light interactions with the fluid mixture at first and second locations along the conduit, wherein the first location is separated by a distance in a direction of flow through the conduit from the second location, and processing first and second time-varying signals of the light interactions detected at the first and second locations, respectively, wherein the processing determines phase velocity of at least one phase within the fluid mixture. For some embodiments, a method of measuring flow of a fluid mixture in a conduit includes measuring light interactions at first and second locations along the conduit to detect a time delay in interactions detected at the first location and then the second, and calculating a velocity of flow within the fluid mixture based on the time delay.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention relate to methods and apparatus that enable direct measurement of at least one flow velocity for one or more phases, individually or in combination, within a multiphase fluid mixture flowing in a conduit. Some embodiments provide determination of actual individual phase flow rates for each of three phases (e.g., oil, water and gas) that are distinct from one another within the fluid mixture. A multiphase flowmeter according to embodiments of the invention includes at least two optical sensors spatially distributed along a length of the conduit and designed to detect light interactions with the fluid mixture unique to the phases such that detected time-varying signals can be processed via cross-correlation or an array processing algorithm to provide desired individual phase flow velocity for oil, water and/or gas phases. This flow velocity can be applied to phase fraction measurements, which can be obtained utilizing the same flowmeter or another separate device, to calculate the flow rates for the phases.

Figure 1:
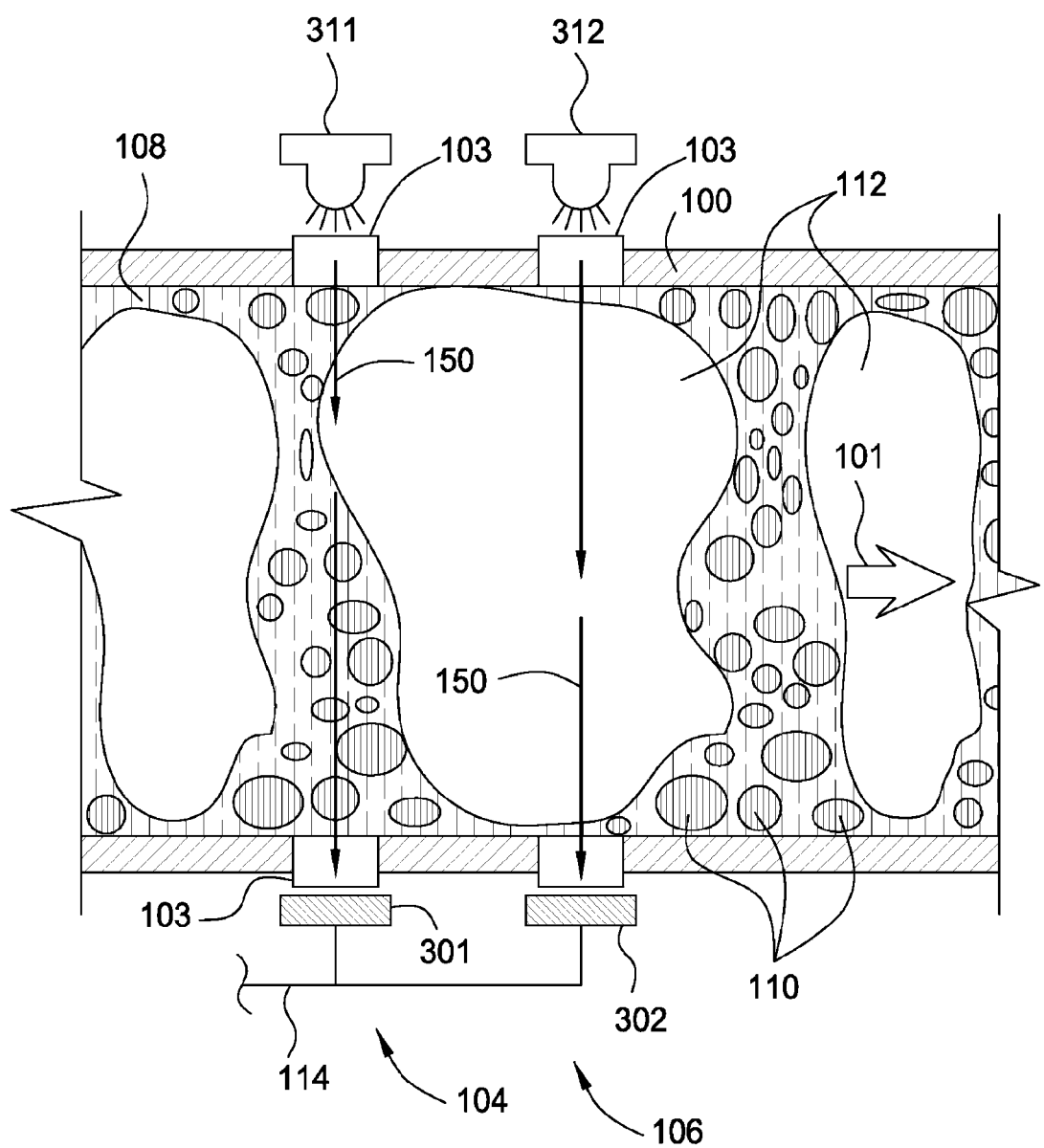
FIG. 1 is a schematic sectional view across a length of conduit having a fluid mixture flowing therein and first and second optical sensing devices spaced along the length, according to embodiments of the invention.

FIG. 1 shows a length of conduit 100 having a first optical sensing device 104 and a second optical sensing device 106 spaced along the length. A fluid flow 101 indicated by an arrow travels through the conduit and can include a water phase 108, an oil phase 110 and a gas phase 112. The water, oil and gas phases 108, 110, 112 remain distinct from one another regardless of various possible flow patterns of this mixture such as a depicted exemplary flow pattern of the phases.

The first optical sensing device 104 includes a first source 311 for introducing light (indicated throughout by arrows 150) into the fluid flow 101 and a first detector 301 to detect the light after being transmitted through the fluid flow 101. Similarly, the second optical sensing device 106 includes a second source 312 for introducing light into the fluid flow 101 and a second detector 302 to detect the light after being transmitted through the fluid flow 101. Windows 103 within the wall of the conduit 100 enable passing the light from each of the sources 311, 312 to corresponding ones of the detectors 301, 302 across the fluid flow 101. Other than being disposed at different locations, the sensing devices 104, 106 can be identical. For some embodiments, the devices 104, 106, individually or collectively, may be the same or similar to one or more of those described in U.S. patent application Ser. No. 11/065,489 (hereinafter referred to as the '489 application) previously incorporated by reference.

The sources 311, 312 can originate from a single emitter that is split or from separate emitters. Further, the sources 311, 312 can include broadband light emitters or one or more narrow band lasers. Each of the phases 108, 110, 112 attenuate the light differently for various wavelengths as the light passes through the fluid flow 101. Accordingly, the detectors 301, 302 measure the light transmitted through the fluid flow 101 for particular individual wavelengths that correspond to the water, oil and gas phases 108, 110, 112. Depending on the sources 311, 312 utilized, appropriate filters coupled with the sources 311, 312 and/or the detectors 301, 302 can discriminate for desired wavelengths.

A communication line 114 coupled to the detectors 301, 302 conveys signals regarding this attenuation of certain wavelengths to processing equipment that analyzes the signals with a cross-correlation or array processing algorithm as described further below. As the basis of this analysis, the water phase 108, for example, within a cross section of the fluid flow 101 at a location of the first sensing device 104 has a unique percentage of the flow, distribution or other property at a given time such that selecting wavelengths for water phase analyses enables detecting the same event of the water phase 108 at a later instant in time with the second sensing device 106 once the fluid flow 101 progresses toward the second sensing device 106. A corresponding analogy applies for the oil phase 110 and the gas phase 112.

Any particular aspect of the fluid flow tends to change or dissipate to some degree as that aspect moves with the fluid flow 101 depending on the coherence of the fluid flow. Advantageously, little appreciable change in the fluid flow 101 occurs between the sensing devices 104, 106 due to selection of spacing between the sensing devices 104, 106. Further, the sensing devices 104, 106 sample at intervals such as several hertz to several kilohertz to provide a depiction of a discrete cross section of the flow without significant averaging of the fluid flow 101 over time, which would tend to obscure time-varying responses to be compared.

Once the time-varying signal(s) is measured for any desired phases within the fluid flow 101, a time delay ($\tau$) can be measured using cross-correlation methods. Velocity of flow for each phases is therefore calculated as being a distance between the sensing devices 104, 106 divided by the time delay ($V=x/\tau$). Alternatively, the flow velocity can be calculated using an array processing algorithm. As mentioned above, differentiation between the phases 108, 110, 112 occurs by the time-varying signal(s) being selected such that it corresponds to one of the phases through, for example, a ratio between two wavelengths detected or one wavelength detected by itself. Attenuation of one wavelength may be substantially dependent on (i.e., sensitive to) a first phase and substantially independent of (i.e., substantially insensitive to) a second phase, while attenuation of another wavelength may be substantially independent of the first phase and substantially dependent on the second phase. A first wavelength band emitted by the sources 311, 312 can be substantially transmitted through a first phase (e.g., the water phase 108) of the fluid flow 101 and substantially absorbed by a second phase (e.g., the oil phase 110), and a second wavelength band emitted by the sources 311, 312 can be substantially absorbed by the first phase relative to the second phase. The detectors 301, 302 can detect attenuation of the first and second wavelength bands upon the infrared radiation passing through at least a portion of the fluid flow 101 such that the time delay $\tau$ is determined based on the attenuation of both the first and second wavelength bands.

Figure 2:
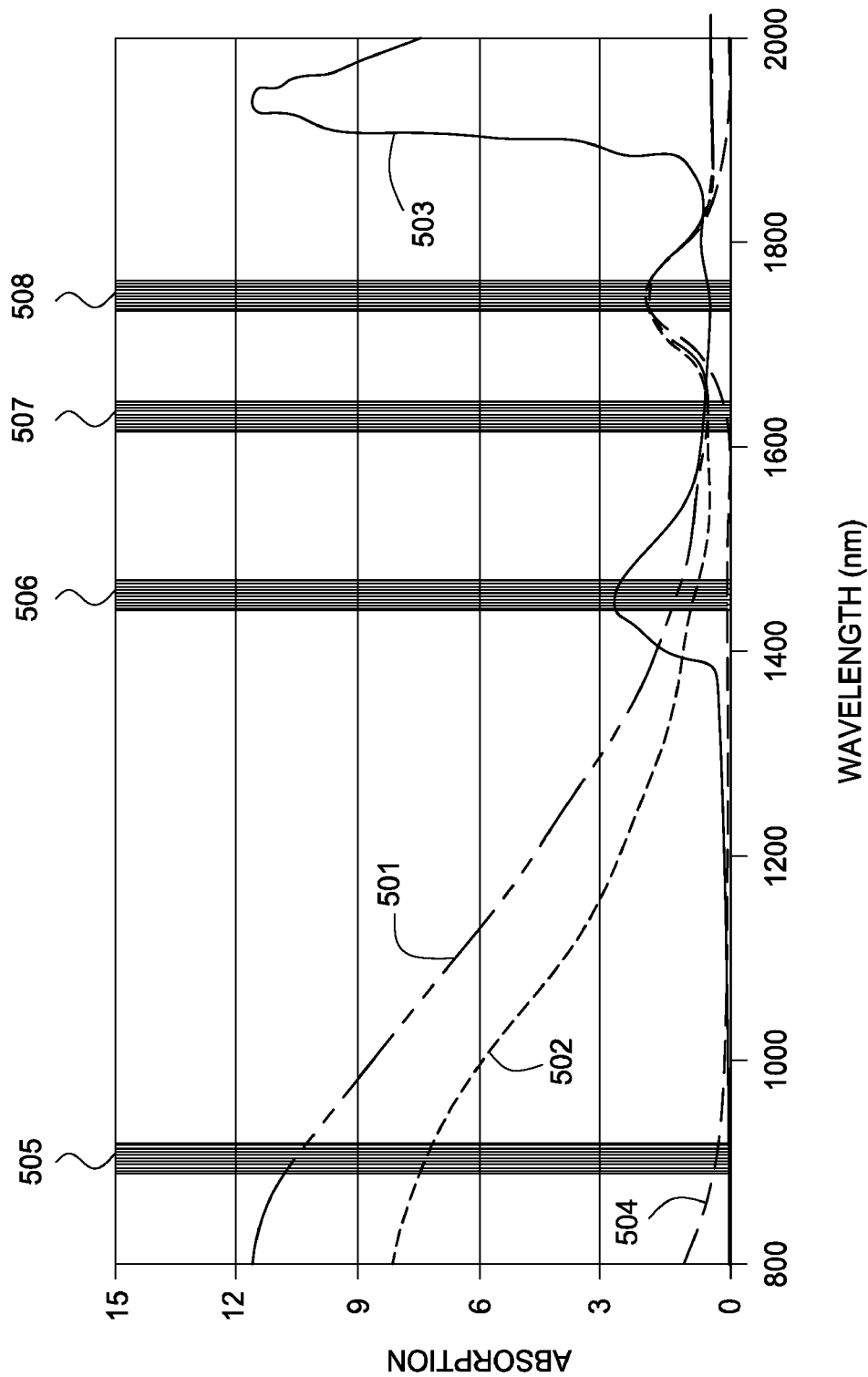
FIG. 2 is a graph illustrating absorption of two types of oil, water and condensate for an infrared region and selected wavelengths, which can be selected for interrogation via the sensing devices shown in FIG. 1.

FIG. 2 illustrates a graph of absorption versus wavelength for two types of oil indicated by curves 501, 502, water represented by curve 503 and condensate denoted by curve 504 for an infrared region. The graph shows four wavelength bands 505-508 for filtering/analysis in determining flow velocities according to embodiments of the invention. Other wavelength bands may be selected without departing from the scope of the invention. In general, a first wavelength band 505 includes wavelengths within a range of approximately 900 nanometers (nm) to 1200 nm, for example about 950 nm, where there is an oil absorbent peak. A second wavelength band 506 includes wavelengths centered around 1450 nm where there is a water absorbent peak. A trough around 1650 nm provides another interrogation region where a third wavelength band 507 generally is centered. A fourth wavelength band 508 generally includes a peak centered about 1730 nm that is fundamentally associated with carbon-hydrogen bonds of the oil 501, 502 and the condensate 504. The substantial similarities and/or differences in the absorbance of the different phases 108, 110, 112 at each of the bands 505-508 further enables their differentiation from one another.

Figure 3:
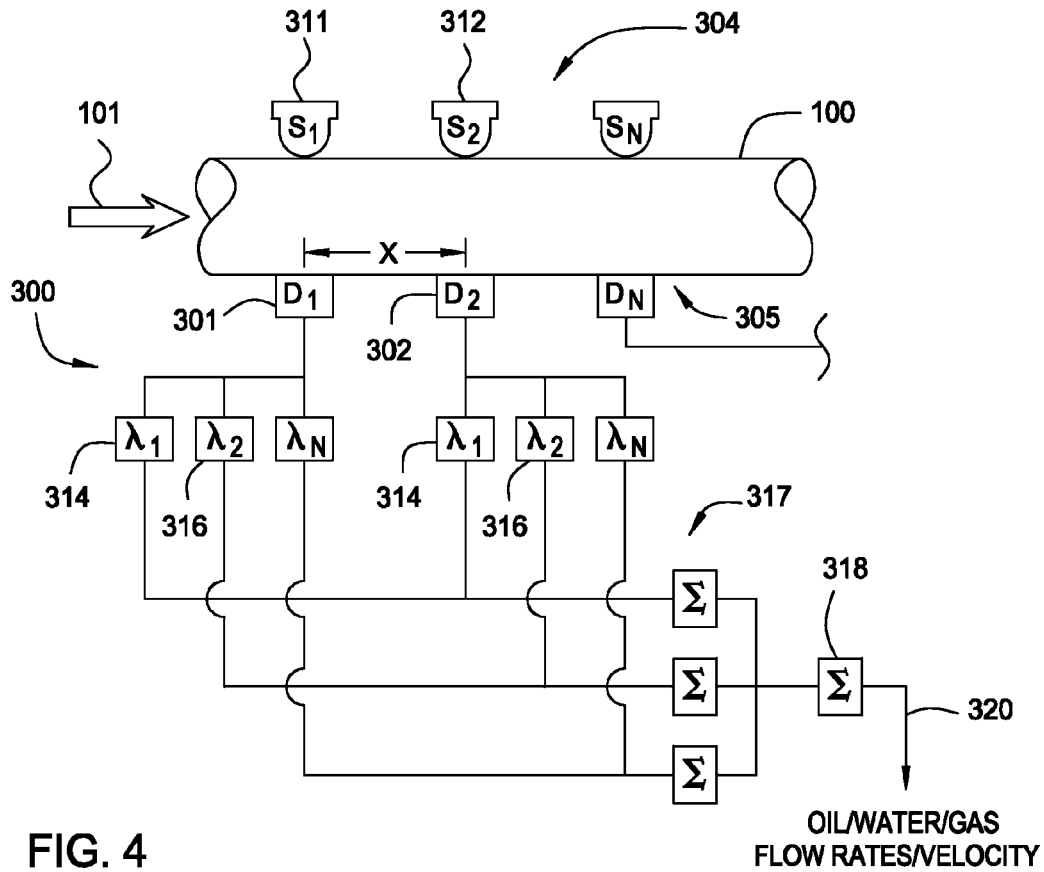
FIG. 3 is a diagram of a distributed array of the optical sensing devices coupled to logic configured to enable calculation of at least one flow velocity of one or more phases within the mixture based on determining a time delay from one sensor to another of certain time-varying properties detected at various wavelengths, according to embodiments of the invention.

FIG. 3 shows a diagram of a flowmeter system 300 utilizing the sources 311, 312 and detectors 301, 302 forming a distributed array 304. The array 304 can include additional sensors and detectors 305, which may be identical or configured to provide different wavelength analysis and/or different spacing. Each detector 301, 302 measures transmittance to provide as output a first wavelength ($\lambda_1$) signal 314, a second wavelength ($\lambda_2$) signal 316 and any additional wavelength ($\lambda_N$) signals. Cross-correlation logic 317 determines the time delay (τ) associated with each of the wavelength signals detected at the detectors 301, 302 as a result of the spacing within the array 304 as indicated by the distance x.

Figure 4:
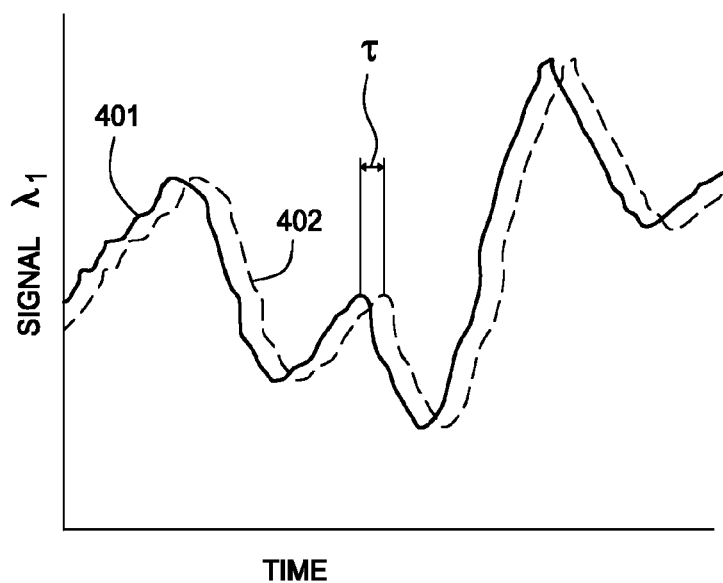
FIG. 4 is a graph of signals detected from the first and second detectors versus time illustrating the time delay ($\tau$).

FIG. 4 shows a graph of a first detected transmittance 401 measured with the first detector along with a second detected transmittance 402 measured by the second detector versus time illustrating the time delay τ between the detected transmittances 401, 402. The detected transmittances 401, 402 represent transmittance of the first wavelength $\lambda_1$ signal 314. For example, the first wavelength $\lambda_1$ can be at 1450 nm such that the time delay τ corresponds to the time required for water within the fluid flow 101 to travel the distance x. For some embodiments, the wavelength signals can be based on a particular wavelength(s) or a ratio of signals from two or more wavelength(s) in view of unique absorption characteristics of phases within the fluid flow 101 such as described above relating to FIG. 2. As examples of this ratio, one wavelength can be selected that is sensitive to gas for comparison with another wavelength selected that is insensitive to gas or other wavelengths sensitive to other constituents of the fluid flow 101.

As illustrated in FIG. 3, flow logic 318 receives input from the cross-correlation logic 317 and provides a flow velocity/rate of at least one of the water, oil and/or gas phases 108, 110, 112, individually or in combination, via an output 320 in the form of a display, printout or other user interface. The flow logic 318 can calculate the velocity (V) for each phase given the distance x and the time delay τ with the formula V=x/τ. As described in the '489 application, the phase fraction of the water, oil and/or gas phases 108, 110, 112 can be calculated. By configuring the array 304 to determine phase fractions as described in the '489 application or utilizing any separate phase fraction meter such as described in the '489 application, individual flow rates for the water, oil and/or gas phases 108, 110, 112 can hence be calculated based on application of respective flow velocities to these phase fractions.

Figure 5:
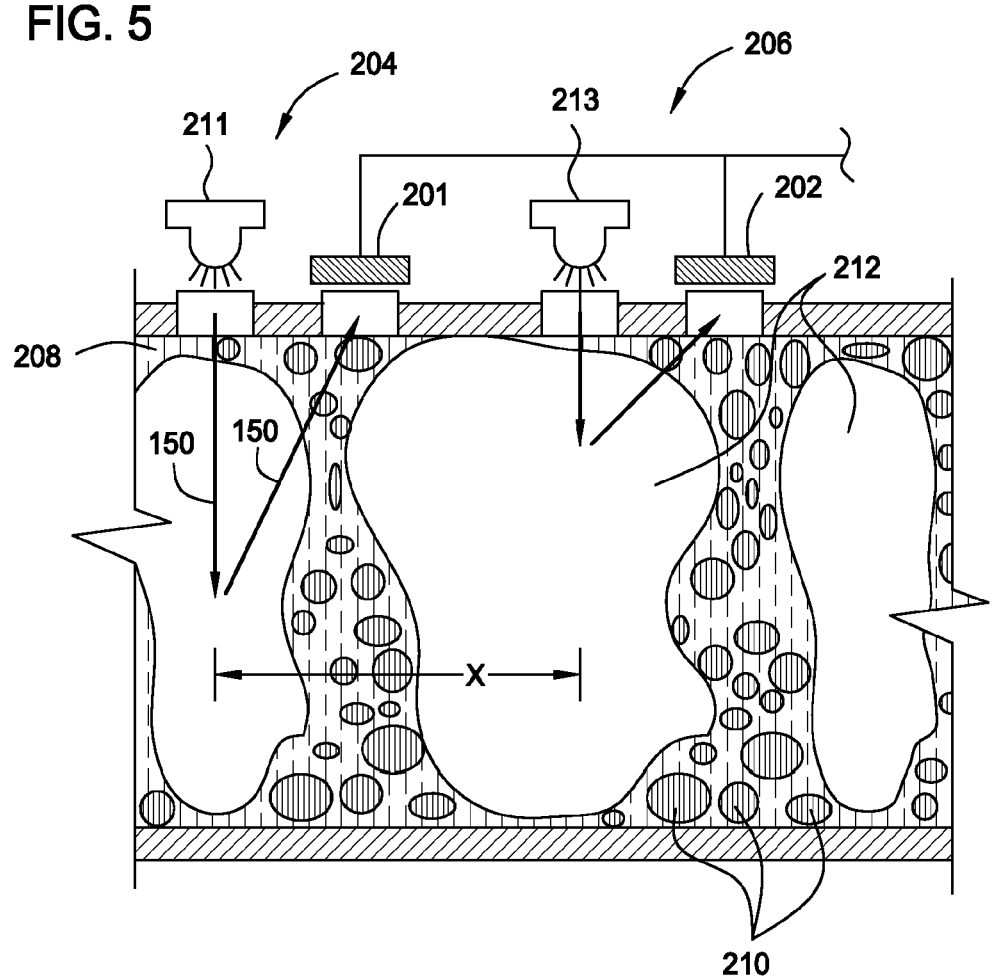
FIG. 5 is a schematic sectional view of first and second reflectance based optical sensing devices for use with some embodiments in similar applications as utilized with transmittance detectors shown in FIGS. 1 and 3.

FIG. 5 shows a schematic sectional view of first and second reflectance based optical sensing devices 204, 206 for use with some embodiments. In similar applications as utilized with transmittance detectors shown in FIGS. 1 and 3, the reflectance based optical sensing devices 204, 206 enable flow velocity/rate determinations. Analogous processing techniques to those previously described herein can be applied to reflected light detected, which is unique to water, oil and gas phases 208, 210, 212. In operation, light emitted by first and second sources 211, 213 reflects off of the water, oil and gas phases 208, 210, 212 and this reflected light is detected at first and second detectors 201, 202, respectively, with certain reflected wavelengths associated with each phase. A time delay τ occurs with the detected reflected light for time-varying reflectance based phenomena traveling with the fluid flow. Therefore, velocity can be calculated as a function of distance between the reflectance based optical sensing devices 204, 206 and time it takes to detect a reflected light feature with the second detector 202 after being detected at the first detector 201. Further, velocity for different ones or combinations of the phases 208, 210, 212 can be calculated depending on which phase(s) the reflected light feature corresponds to given the wavelength(s) measured at the detectors 201, 202.

Figure 6:
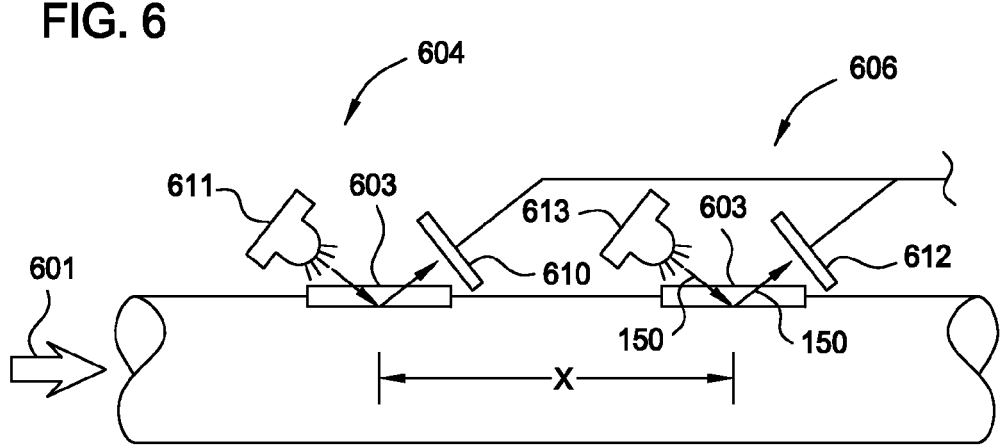
FIG. 6 is a schematic view of first and second attenuated total reflection and/or refractive index based optical sensing devices for use with some embodiments according to techniques such as applied with transmittance detectors shown in FIGS. 1 and 3.

FIG. 6 illustrates a schematic sectional view of first and second refractometers 604, 606 for use with some embodiments. The refractometers 604, 606 can enable refractometry and attenuated total reflectance (ATR) spectrometry by measuring the refractive index of fluids and/or attenuated reflectance spectra. A fluid flow 601 exposed at windows 603 to first and second light sources 611, 613 disposed at an angle with respect to correspondingly angled detectors 610, 612 provides varying refractive indices based on constituents of the fluid flow 601. The windows 603 have a refractive index of about 1.7, for example, such that light transmitted through the windows reflects at an interface between the window 603 and the fluid flow 601 due to differences in the refractive indices of the windows and the fluid flow. Further, some light is absorbed by the constituents of the fluid flow 601 at this interface such that attenuation characteristics of the light reflected differs depending on absorbency of these constituents. While the windows 603 in this and other illustrated embodiments are shown separate, some embodiments can integrate the windows utilizing a single window for more than one sensing device such as the refractometers 604, 606. The detectors 610, 612 measure increases in reflections such as when the refractive index of the fluid flow 601 decreases. An oil phase having a refractive index of about 1.5 gives rise to a reflected fraction of light from the sources 611, 613 which, for example, is less than 20%. However, a water fraction with a refractive index typically in the range 1.3 to 1.4 produces a reflected fraction of the light that is about 30-65% while gas with a refractive index close to 1.0 provides a reflected fraction of the light approaching 100%.

Time-varying signals within corresponding strengths of reflected signals detected for the different phases can be determined by analyzing responses from the first and second detectors 610, 612. Respective time delays occur with the detected reflected light for these strengths of the reflected signals enabling differentiation of a time delay τ for each phase. Therefore, velocity can be calculated as a function of distance between the refractometers 604, 606 and time it takes to detect a refractive index characteristic of one phase at the second detector 612 after being detected at the first detector 610.

Embodiments illustrated provide non-intrusive flow velocity/rate analysis techniques. For example, the first source 311 is disposed outside the conduit 100 and opposite the first detector 301 also located outside the conduit such that the transmission or absorption measurements are full-bore across a cross section of the conduit 100. Some embodiments however can be implemented as an intrusive probe as illustrated, for example, in the '489 application previously incorporated by reference.

While the foregoing is directed to embodiments of the present invention, other and further embodiments of the invention may be devised without departing from the basic scope thereof, and the scope thereof is determined by the claims that follow.

What is claimed is:

1. An apparatus for measuring flow of a fluid mixture in a conduit, comprising:
    at least one light source for transmitting light into the fluid mixture;
    first and second optical sensors disposed along the conduit and configured to detect light interactions with the fluid mixture, wherein the first optical sensor is separated by a distance in a direction of flow through the conduit from the second optical sensor, wherein the light interactions detected by the optical sensors are a measure of reflectance of the light transmitted into the fluid mixture, and wherein the light source is on a same side of the conduit as the first and second optical sensors; and
    a processor coupled to receive first and second time-varying signals of the light interactions from the first and second optical sensors, respectively, wherein the processor is configured with logic to determine phase velocity of at least one phase within the fluid mixture.

2. The apparatus of claim 1, wherein the logic calculates a time delay of corresponding responses within the first and second time-varying signals.

3. The apparatus of claim 1, wherein the logic determines the phase velocity based on the distance divided by the time delay.

4. The apparatus of claim 1, wherein the optical sensors form refractometers.

5. The apparatus of claim 1, wherein each of the sensors is disposed non-intrusively outside of the conduit.

6. The apparatus of claim 1, wherein the logic is further configured to determine individual phase velocities for each of three distinct phases within the fluid mixture.

7. The apparatus of claim 1, wherein the first and second time-varying signals correspond to wavelength signals selectively responsive to the at least one phase.

8. The apparatus of claim 1, wherein the logic is further configured to determine phase flow rate of the at least one phase given a phase fraction of the at least one phase.

9. The apparatus of claim 1, wherein the logic comprises a cross-correlation algorithm.

10. The apparatus of claim 1, wherein:
the light source is configured to emit into the fluid mixture infrared radiation that includes at least first and second wavelength bands, the first wavelength band substantially transmitted through a first phase of the fluid mixture and substantially absorbed by a second phase, and the second wavelength band substantially absorbed by the first phase relative to the second phase; and
at least one of the first and second optical sensors is configured to provide the time varying signals based on detection of attenuation of the first and second wavelength bands upon the infrared radiation passing through at least a portion of the fluid mixture.

11. A method of measuring flow of a fluid mixture in a conduit, comprising:
transmitting light into the fluid mixture;
detecting light interactions with the fluid mixture at first and second locations along the conduit, wherein the first location is separated by a distance in a direction of flow through the conduit from the second location, wherein the light is transmitted into the fluid mixture on a same side of the conduit as the first and second locations, and wherein the light interactions detected at the first and second locations are a measure of reflectance of the light transmitted into the fluid mixture; and
processing first and second time-varying signals of the light interactions detected at the first and second locations, respectively, wherein the processing determines phase velocity of at least one phase within the fluid mixture.

12. The method of claim 11, wherein the processing comprises calculating a time delay of corresponding responses within the first and second time-varying signals.

13. The method of claim 12, wherein the processing determines the phase velocity based on the distance divided by the time delay.

14. The method of claim 11, wherein the processing determines individual phase velocities for each of three distinct phases within the fluid mixture.

15. The method of claim 11, wherein the detecting the light interactions comprises measuring reflectance of light transmitted into the fluid mixture to provide the first and second time-varying signals corresponding to wavelength signals selectively responsive to the at least one phase.

16. The method of claim 11, further comprising:
determining a phase fraction of the at least one phase; and
calculating a phase flow rate of the at least one phase utilizing the phase velocity and the phase fraction as determined.

17. A method of measuring flow of a fluid mixture in a conduit, comprising:
transmitting light into the fluid mixture;
measuring light interactions at first and second locations along the conduit to detect a time delay in interactions detected at the first location and then the second, wherein the light is transmitted into the fluid mixture on a same side of the conduit as the first and second locations and wherein the light interactions detected are a measure of reflectance of light transmitted into the fluid mixture; and
calculating a velocity of flow within the fluid mixture based on the time delay.

18. The method of claim 17, further comprising:
determining a phase fraction within the fluid mixture; and
calculating a phase flow rate utilizing the velocity and the phase fraction.

* * * * *